United States Patent
Kourtidis et al.

(10) Patent No.: US 6,393,673 B1
(45) Date of Patent: May 28, 2002

(54) MECHANICAL-FASTENING ELEMENT

(75) Inventors: Konstantinos Kourtidis; Rolf Preissel, both of Duesseldorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/463,935

(22) PCT Filed: Jul. 30, 1998

(86) PCT No.: PCT/US98/15745

§ 371 (c)(1),
(2), (4) Date: Apr. 29, 2000

(87) PCT Pub. No.: WO99/05929

PCT Pub. Date: Feb. 11, 1999

(30) Foreign Application Priority Data

Jul. 31, 1997 (EP) .............................. 97113183

(51) Int. Cl.[7] .............................................. A44B 18/00
(52) U.S. Cl. ........................................... 24/304; 24/306
(58) Field of Search ........................ 24/442, 306, 304, 24/DIG. 11; 604/391

(56) References Cited

U.S. PATENT DOCUMENTS

| | | | |
|---|---|---|---|
| 3,192,589 A | 7/1965 | Pearson ....................... | 24/204 |
| 3,594,965 A | 7/1971 | Saether ........................ | 52/126 |
| 3,718,725 A | 2/1973 | Hamano ..................... | 264/163 |
| 4,290,174 A | 9/1981 | Kalleberg .................... | 24/204 |
| 4,794,028 A | 12/1988 | Fischer ....................... | 428/100 |
| 4,894,060 A | 1/1990 | Nestegard ................... | 604/391 |
| 4,984,060 A | 1/1991 | Ohmi et al. ................. | 357/68 |
| 4,994,060 A | 2/1991 | Rink et al. .................... | 606/28 |
| 4,994,339 A | 2/1991 | Kinoshita et al. ............. | 430/78 |
| 5,077,870 A | 1/1992 | Melbye et al. ................ | 24/452 |
| 5,077,970 A | 1/1992 | Hamburg ..................... | 60/274 |
| 5,315,740 A | 5/1994 | Provost ....................... | 24/452 |
| 5,607,635 A | 3/1997 | Melbye et al. ............... | 264/169 |
| 5,620,769 A | 4/1997 | Wessels et al. ............. | 428/100 |
| 5,636,414 A | 6/1997 | Litchholt ..................... | 24/304 |
| 6,054,091 A | 4/2000 | Miller et al. ................. | 264/442 |

FOREIGN PATENT DOCUMENTS

| | | |
|---|---|---|
| EP | 0 321 232 B1 | 6/1989 |
| EP | 0 321 234 B2 | 6/1989 |
| EP | 0 529 681 B1 | 3/1993 |
| JP | 98993 | 9/1997 |
| WO | WO92/04839 | 4/1992 |
| WO | WO93/13147 | 7/1993 |
| WO | WO93/13148 | 7/1993 |
| WO | WO94/23610 | 10/1994 |

Primary Examiner—James R. Brittain
(74) Attorney, Agent, or Firm—Gary L. Griswold; Robert W. Sprague; William J. Bond

(57) ABSTRACT

The invention relates to a mechanical fastening element comprising a multiplicity of flexible hook elements emanating from a backing layer (1) and comprising stems (2) terminating in hook heads (3), said fastening element being releasably engageable with a complementary mechanical fastening element, the top portions of the hook heads (3) and/or at least part of the interstitial spaces (4) between the stems (2) of said fastening means being coated with a hot-melt pressure-sensitive adhesive (5) so that the level of the adhesive in the interstitial spaces (4), where present, does not exceed the length of the stems (2), and so that essentially no adhesive bridges are present between adjacent hook heads (3), said hot-melt pressure sensitive adhesive (5) having a viscosity as measured at the coating temperature of between 2,000 and 18,000 mPa-s.

7 Claims, 2 Drawing Sheets

MECHANICAL-FASTENING ELEMENT

FIELD OF THE INVENTION

The present invention relates to a mechanical hook fastening element comprising a multiplicity of flexible hook elements emanating from a backing layer and comprising stems terminating in hook heads, said fastening element being releasably engagable with a complementary mechanical fastening element, the top portions of at least some hook heads and/or at least part of the interstitial spaces between the stems of said fastening means being covered with a pressure-sensitive adhesive. The invention also refers to a method of preparing said fastening element and to its use in absorbent articles such as disposable diapers.

BACKGROUND OF THE INVENTION

Hook-and-loop fastening systems comprising a hook fastening element and a loop fastening element are widely used for a vast array of products and applications. More specifically, hook-and-loop fastening systems can be used for releasably closing garments, for example, disposable garments such as diapers or hospital gowns. There is a wide variety of methods of forming hook fastening elements for use in hook-and-loop fastening systems. Depending on the geometrical form of the hook and/or loop elements, the hook elements have different engagement mechanisms and characteristics with mating loop materials.

The hook fastening element described in U.S. Pat. No. 3,718,725 is made from a fabric having an orderly array of upstanding loops. After inserting rods into rows of loops to maintain their upstanding position, platens or rollers apply heat and pressure to melt each loop and its summit and to press each free molten end to form a knob or head that can interengage with the loop element of a hook-and-loop fastening system. Because the knobs or heads afford a mushroom appearance, this type of hook fastening is called "mushroom-type". Mushroom-type hook fastening elements are also described, for example, in WO 94/23,610 and U.S. Pat. No. 5,077,970.

J-shaped hook fastening elements are described, for example, in U.S. Pat. No. 3,594,965, U.S. Pat. No. 4,994, 339 and U.S. Pat. No. 5,315,740. The hook elements have a profile defined by an inner smooth contoured, generally concave face and a generally convex shaped outer face. The hook described in these patents tapers smoothly and continuously in width from the hook base to the hook free end. The hook element is allegedly designed so that it will not deform to release a loop engaged with the hook in shear mode or at a desired applied force.

A wide variety of sizes and shapes of hook elements are described in WO 94/23,610, WO 92/04,839 and U.S. Ser. No. 08/723,632 filed by the present applicant. Using methods described in these patent applications, a backing having a large number of upstanding thermoplastic stems is fed through a gap between a nip formed by, for example, two calendar rolls. The upper nip is smooth and heated so that the distal ends or tips of the stems are deformed under heat and mechanical pressure, forming various types of cap structures depending on the nip conditions selected, the relative speed of the stems in the nip, and the size and shape of the stems. The undeformed stem portion and the deformed cap together form a hook element.

U.S. Pat. No. 4,894,060 describes a hook fastening element comprising a thin strong flexible plate like backing, and a multiplicity of resiliently flexible spaced hook elements projecting at an essentially night angle from the upper surface of the backing. The hook elements each comprise a stem portion attached at one end of the backing, and a head portion at the end of the stem stem portion opposite the backing. The head portion projects past the stem portion on at least one of two opposite sides, and has a rounded surface opposite the stem portion to help the head portion enter between loops in a loop fastener element. U.S. Pat. No. 4,984,060 describes J- and T-shaped hooks as well as more complicated geometrical forms. J-shaped hook fastening elements are also described in U.S. Pat. No. 4,794,028 and U.S. Pat. No. 5,620,769.

Although a hook fastening element is typically sold with a complementary loop fastening element, the hook fastening element can also be used by itself to become releasably fastened to fabrics that can be easily penetrated by the hook elements. Mushroom-type and/or—appropriately sized hook fastening elements can, for example, be described to become releasably fastened to burlap, terry cloth and tricot. Mushroom-type hook fastening elements can also be designed so that two hook fastening elements can be used to fasten two articles together by adhering each hook fastening element to one of the articles and then interengaging the two fastening elements. Interengagable mushroom-type hook fastening elements are described, for example, in U.S. Pat. No. 3,192,589 or U.S. Pat. No. 4,290,174.

Mechanical hook-and-loop fastening systems have been proposed for use in disposable garment closure systems such as, for example, diapers and hospital gowns because the hook-and-loop system is unaffected by contaminations with, for example, talcum powder or baby oil which may destroy the holding power of pressure-sensitive adhesive closure systems. Mechanical hook-and-loop fastening systems, however, do not provide a disposal mechanism by which the soiled absorbent article may be folded or rolled up after use into a configuration for disposal, secured in the disposal configuration and conveniently thrown away. EP 0,321,232 therefore suggests closure tabs for disposable absorbent articles, particularly diapers, comprising a mechanical hook fastening element and additionally an adhesive fastening element on a second area of the closure tab of the closure system. While the mechanical hook fastening element is engagable with a complementary mechanical loop fastening element on the landing zone of the diaper and thus secures the diaper to the wearer's body during use, the adhesive fastening element can adhere to the outside surface of the diaper when it is rolled up for disposal. Due to the additional adhesive securement means, the closure tab exhibits. however, an extended length which is not fully satisfactory from a design and cost point of view. EP 0,321,234 suggests to attach a third mechanical closure system to the body portion of the absorbent article which is engagable with the mechanical hook fastening element on the closure tab, thus providing a disposal means. Other solutions are disclosed, for example, in EP 0,529,681 including closure tabs comprising a hook fastening tab and an additional adhesive fastening element which could be, e.g. subjacent to the hook element on the fastening element or a separate adhesive fastening tab. The constructions of EP 0,321,234 and EP 0,529,691 are, however, relatively complicated and typically require explanation to the user.

It was therefore an object of the present invention to provide a mechanical hook fastening element offering in addition to the mechanical fastening mechanism an adhesive fastening mechanism to increase the versatility of said mechanical hook fastening element, It was another object of the present invention to provide a hook and loop mechanical closure system for disposable garments having a disposability feature. Other objects of the present invention can easily be taken by the person skilled in the art from the following detailed specification.

BRIEF DESCRIPTION OF THE INVENTION

The present invention relates to a mechanical fastening element comprising a multiplicity of flexible hook elements emanating from a backing layer 1 and comprising stems 2 terminating in hook heads 3, said fastening element being releasable engagable with a complementary mechanical fastening element. Top portions of at least some hook heads and/or at least part of the interstitial spaces 4 between the stems 2 of said fastening element being coated with a hot-melt pressure-sensitive adhesive 5 so that the level of the adhesive in the interstitial spaces 4, where present, does not exceed the length of the stems 2. Also essentially no adhesive bridges are present between adjacent hook heads 3. The hot-melt pressure sensitive adhesive has a viscosity as measured at the coating temperature of between 2,000 and 18,000 mPa-s.

The present invention furthermore relates to a method of manufacturing a mechanical fastening element according to the invention, said method comprising passing a continuous sheet 7 of a mechanical fastening element comprising a multiplicity of flexible hook elements emanating from a backing layer 1 and comprising stems 2 terminating in hook heads 3, by a coating head 6 with the hook heads 3 facing the coating head 6, applying a hot-melt pressure sensitive adhesive having a viscosity as measured at the coating temperature of between 2,000 and 18,000 mPa-s, to the continuous sheet 7 by means of the coating head 6, orienting the coating head 6 with respect to the continuous sheet 7 of the mechanical fastening element so that the hot-melt pressure sensitive adhesive is coated onto at least part of the hook heads 3 and/or at least into part of the interstitial room 4 between the stems 2 of said fastening means so that the level of the adhesive in the interstitial rooms 4 where present does not exceed the length of the stems 2 and essentially no adhesive bridges are present between the heads.

The present invention furthermore relates to an absorbent article, in particular a disposable diaper, comprising a closure tab on each edge portion of the diaper comprising a first mechanical fastening element according to claim 1, said first mechanical fastening element being releasably engagable with a second mechanical fastening on the landing zone of the outside surface of the diaper which is complementary with the first mechanical fastening element, said first mechanical fastening element being adhesively and/or mechanically attachable to other portions of the outside surface of the diaper or to a third mechanical fastening element on the surface of the diaper or on the other closure tab whereby the third mechanical outs) fastening means is complementary with the first mechanical fastening element, said adhesive attachment being obtained by means of the hot-melt pressure-sensitive adhesive (5) present on at least part of the hook heads (3) and/or in at least part of the interstitial spaces (4) between the stems (2) of said first mechanical fastening element and said mechanical attachment being obtained by mechanically engaging the first mechanical fastening element with the outside surface of the diaper or the third mechanical fastening element.

The present invention furthermore relates to a closure tab for an absorbent article, particularly for a disposable diaper, for fastening the article onto the body of a person, said tab comprising a mechanical fastening means according to the invention.

DETAILED DESCRIPTION OF THE INVENTION

Figure 1:
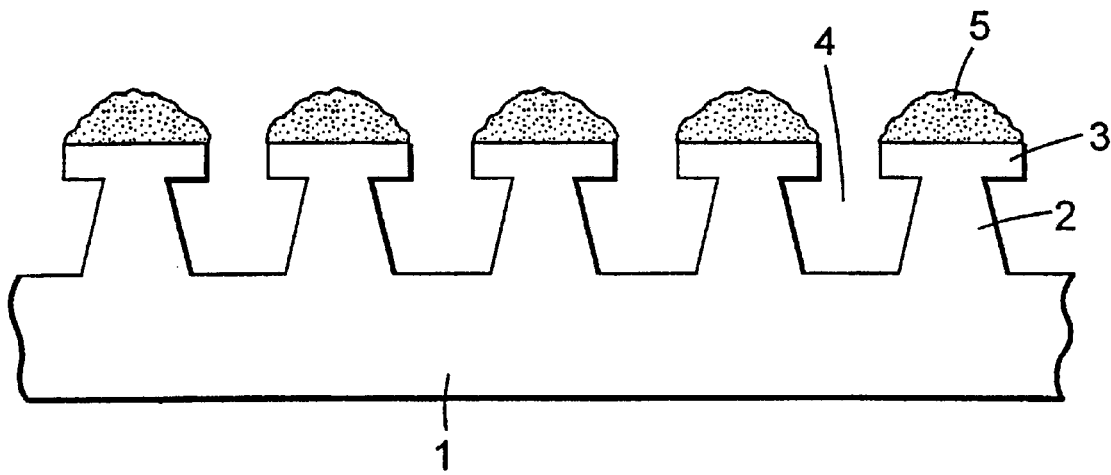
FIG. 1 shows a schematic representation of a hook fastening element according to the invention having flexible hook elements emanating from a backing layer 1 and comprising stems 2 terminating in hook heads 3 with the of top portions of at least some hook heads 3 being covered with a hot-melt pressure-sensitive adhesive 5 whereas the interstitial spaces 4 between adjacent stems are essentially free from the adhesive.

The mechanical hook fastening elements useful in the present invitation comprise a multiplicity of flexible hook elements emanating from a backing layer 1 and comprising stems 2 terminating in hook heads 3.

The geometrical shape of the hook heads is not particularly limited and comprises the variety of shapes described in the literature. The hook head projects past the stem 2 portion in at least one direction to provide for effective and reliable engagability with the complementary mechanical loop fastening element. The ratio of the maximum diameter of the hook head over the diameter of the stem 2 at its upper and preferably is at least 1.025, more preferably at least 1.05 and especially preferably of at least 1.2. The hook heads preferably comprise a relatively flat or planar upper surface which renders the hook fastening element skin friendly and non-abrasive, imparts a film-like texture to them and, in particular, facilities and supports transfer and retention of the hot-melt adhesive 5. In a preferred embodiment, the ratio of the essentially flat or planar upper surface of the hook head 3 with respect to its maximum diameter preferably is at least 40% and more preferably at least 50%.

The stem 2 may have an essentially circular cross-section but other shapes such as, for example, essentially triangular or rectangular cross-sections or less regular cross-sections are also possible. The thickness of the stem 2 along its vertical extension from the backing layer 1 to the hook head 3 may be essentially constant but may also vary whereby an essentially constant thickness or a thickness essentially decreasing from the backing layer 1 to the hook head 3, are preferred.

The size of the hook elements can vary over a broad range. For use in disposable garments such as diapers or hospital gowns, the hook elements preferably are of essentially uniform height, preferably from about 0.10 to 1.3 mm in height, and more preferably from about 0.2 to 0.5 mm in height. The stems 2 have a diameter adjacent to the hook head of preferably from 0.07 to 0.7 mm and more preferably from about 0.1 to 0.3 mm. The hook heads preferably project radially past the stems 2 in at least one direction by, in average, about 0.02 to 0.25 mm. The maximum thickness of the hook heads 3 as measured in a direction parallel to the axis of the stems 2 between their outer and inner surfaces, preferably is from about 0.01 to 0.3 mm and more preferably from about 0.02 to 0.1 mm. The hook heads 3 preferably have an average maximum diameter to average maximum thickness ratio preferably from 1.5:1 to 12:1, and more preferably from 2.5:1 to 6:1.

The mechanical hook fastening element useful in the present invention can be prepared by weaving techniques or extrusion molding with extrusion molding being preferred. Virtually any orientable thermoplastic resin that is suitable for extrusion molding may be used. Preferred thermoplastic resins include, for example, polyesters such as poly(ethylene terephthalate), polyamides such as nylon, poly(styrene-acrylonitrile), poly(acrylonitrile-butadione-styrene), poly-olefins such as polypropylene, and plasticized polyvinyl chloride. Preferably the resin is a polypropylene/polyethylene copolymer or a blend of polypropylene with an ethylene-vinyl acetate block copolymer or a styrene-ethylene-butylenestyrene block copolymer. A preferred thermoplastic resin is a random copolymer of polypropylene and polyethylene containing 4% polyethylene and having a melt flow index of 7.0. available as WRS-6-165 from Union Carbide Company, Danbury, Conn., U.S.A. To have good flexibility and strength, the backing layer 1 of the mechanical hook fastening element preferably is a film from 0.02 to 0.5 mm in thickness, and more preferably is from 0.06 to 0.3 nun thick, especially when the fastener is made of polypropylene or a copolymer of propylene and ethylene. For some applications, a stiffer backing can be used, or the backing can be coated with a layer of a pressure-sensitive adhesive on its surface opposite the surface with the hook elements, by which the backing layer 1 could be adhered to a substrate.

The mechanical hook fastening elements useful in the present invention can be prepared using various techniques and, in particular. extrusion molding techniques described in the state-of-the-art. Particularly useful are the extrusion molding techniques described in WO 94/23,610, U.S. Pat. No. 5,607,635, U.S. Pat. No. 5,077,870, U.S. Pat. No. 4,994,060, U.S. Pat. No. 5,620,769, U.S. Pat. No. 4,794,028, WO 94/04,839 and U.S. Ser. No. 08/723,632 filed by the present applicant.

In order to impart an additional adhesive fastening functionality to the mechanical hook fastening element it is required to apply a pressure-sensitive adhesive to the hook elements essentially forming no adhesive bridges between adjacent hook heads. The term "essentially no adhesive bridges" means that adhesive bridges are present to a degree only so that when contacting the adhesive coated mechanical hook fastening element with a complementary mechanical fastening element engagable with the uncoated mechanical hook fastening element, it is still engagable with the complementary mechanical fastening element, and the hook fastening element and the complementary fastening element still work as mechanical fastening system. The term "essentially no adhesive bridges" preferably means that only 15% or less, more preferably 10% or less and particularly preferably 5% or less of adjacent hook heads are connected with adhesive bridges.

FIG. 1 schematically shows a preferred embodiment of a mechanical hook fastening element according to the present invention comprising hook elements emanating from a backing layer 1 and comprising stems 2 terminating in hook heads 3 whereby the pressure-sensitive adhesive 5 is deposited essentially on the top portions of the hook heads 3. In this configuration, the engagability of the hook elements with a complementary mechanical fastening element is not adversely affected, and the additional adhesive functionality is obtained through the pressure-sensitive adhesive deposited on part of the top portions of the hook heads.

Figure 2:
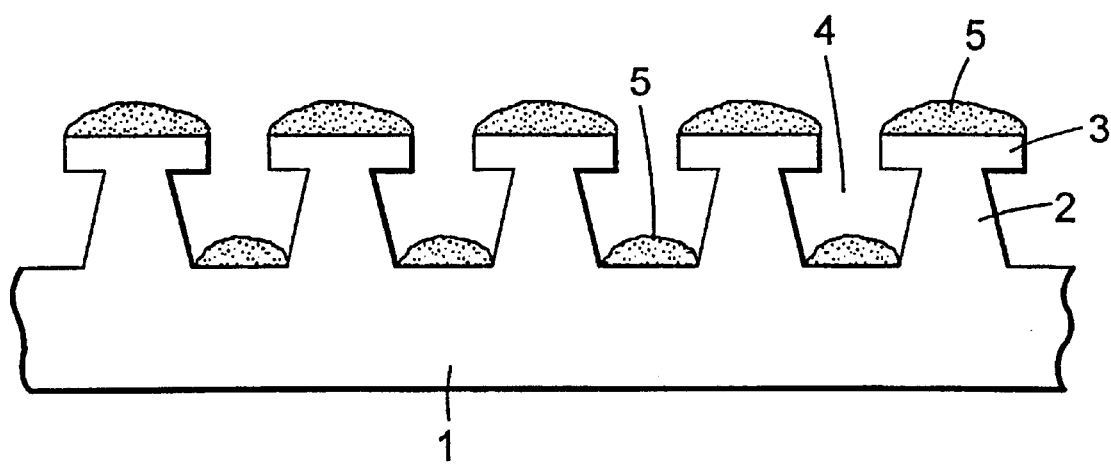
FIG. 2 shows a schematic representation of a mechanical hook fastening element according to the invention having flexible hook elements emanating from a backing layer 1 and comprising stems 2 terminating in hook heads 3 with the top portions of at least some hook heads 3 and the interstitial spaces 4 between adjacent stems being covered with a hot-melt pressure-sensitive adhesives.

FIG. 2 schematically shows another preferred embodiment of the mechanical hook fastening element according to the invention comprising pressure-sensitive adhesive 5 being deposited on the top portions of the hook heads 3, and in the interstitial spaces 4 between adjacent stems 2. The level of the pressure-sensitive adhesive 5 in the interstitial spaces 4 does not exceed the length of the stems in order not to adversely affect the engagability of the hook heads 3 with the complementary mechanical fastening element. Preferably, the level of the pressure-sensitive adhesive in the interstitial spaces 4 is on average less then 60% of the length of the stems 2.

It is to be understood that FIGS. 1 and 2 are schematic representations only and that a wide variety of other configurations of the pressure-sensitive adhesive bearing the mechanical hook fastening element of the present invention is possible. In other preferred embodiments, only the top portions of some of the hook heads 3 and/or only part of the interstitial spaces 4 between the stems 2 may be coated with a pressure-sensitive adhesive 5 whereby it is possible, for example, that the top portions of some of the hook heads 3 and part of the corresponding interstitial spaces 4 are coated simultaneously. It is also possible, for example, that at least part of the interstitial spaces 4 between the stems 2 are coated with the pressure-sensitive adhesive 5 whereas the corresponding hook heads 3 are essentially free from pressure-sensitive adhesive.

The level of the pressure-sensitive adhesive deposit in the interstitial spaces 4 can be less regular and vary considerably between adjacent stems. It is, however, also possible, to obtain a gradually increasing or decreasing level of the pressure-sensitive adhesive 5 in the interstitial spaces 4 between the stems along the longitudinal extension of the mechanical fastener element in cross and/or machine direction. Likewise, the height of the pressure-sensitive adhesive layer on top of the hook heads 3 can vary over the longitudinal extension of the mechanical fastener element. The pressure-sensitive adhesive layer 5 may fully cover the hook heads 3 as is indicated in FIGS. 1 and 2 but it is also possible that the pressure-sensitive adhesive layer 5 Is essentially deposited for other hook head geometries on the essentially flat and planar part of the hook heads, only.

It was found by the present inventors that avoiding of the formation of bridges between adjacent hook heads 3 and/or controlling of the level of the pressure-sensitive adhesive 5 in the interstitial spaces 4 between the stems 2 requires using a pressure-sensitive hot-melt adhesive having a viscosity at the coating temperature as measured according to DIN 53018 of between 2,000 and 18,000 mPa-s, more preferably of between 5,000 and 15,000 mPa-s and essentially preferably of between 7,000 and 12,000 mPa-s. It was found that for viscosities less than 2.000 mpa-s the flow of the molten pressure-sensitive adhesives onto the hook heads 3 and/or into the interstitial spaces 4 is difficult to control. For viscosities of more than 10,000, the adhesive 5 typically forms irregular clots covering larger areas of the hook structure or even fully covers the hook structure, thus at least partly destroying the mechanical fastening functionality.

It was furthermore found that the hot-melt pressure-sensitive adhesives useful in the present invention are preferably selected to exhibit a 180° peel adhesion as measured according to PSTC-1 using a 36 μm continuous polyester film homogenously coated with the respective hot-melt pressure-sensitive adhesive at a coating weight of 20 g/m$^2$ and a stainless steel substrate, of between 10 and 50 N/25 mm and more preferably of between 15 and 45 N/25 mm. When using the hot-melt pressure-sensitive adhesive bearing hook fastening elements of the present invention in closure tabs of disposable garments, the disposable garment is releasably secured to the wearer's body by mechanically engaging the hook fastening element of the closure tab with a complementary mechanical fastening element forming the landing zone on the outside surface of the disposable garment. Fastening of the diaper during use may additionally be improved by the adhesive fastening functionality of the hook fastening element which is imparted by the hot-melt pressure-sensitive adhesive. The adhesive fastening functionality is also used, optionally in combination with the mechanical fastening functionality of the hook fastening element, when rolling up the soiled garment and securing It for disposal. It was found by the present inventors that if the hot-melt pressure-sensitive adhesive is too aggressive, the hot-melt pressure-sensitive adhesive coating an the hook heads and/or in the interstitial spaces 4 between the stems 2 tend to become destroyed and/or disrupted from the hook fastening element when securing the diaper to the wearer's body during use, This results in deterioration of the adhesive fastening functionality of the mechanical fastening element on the closure tab of the disposable garment. The present inventors found that the aggressiveness of the hot-melt pressure-sensitive adhesive is reliably reflected by its 180° peel adhesion measured as described above. An upper limit of the 180° peel adhesion measured as described above of 50 N/25 mm is also preferred in order to allow, for example, for releasably adhering the adhesive coated mechanical fastening element to the release liner of the closure tab which secures the closure tab to the inner surface of the edge portion of the diaper, when storing the diaper prior to its use, In case the outside surface of the diaper is formed by a polymeric film, the adhesive coated mechanical fastening element can preferably be adhesively adhered to the outside surface of the diaper, in particular in case the top portion of at least some hook heads 3 are coated with the hot-melt pressure sensitive adhesive. In this case, the 180° peel adhesion measured as described above preferably is at least 10 N/25 mm in order to allow, for example, the diaper to be reliably secured for disposal. The hot-melt pressure-sensitive adhesives 5 useful in the present invention may preferably be selected from a group of adhesives comprising resin tackified synthetic rubber adhesives such as, in particular, styrene-butadiene rubbers, butyl rubbers and AB-A block copolymers such as styrene-isoprene-styrene block copolymers or styrenebutadiene-styrene block copolymers and resin tackified natural rubber adhesives. Acrylate-based hot-melt pressure-sensitive adhesives like those disclosed in WO 93/13,147 and WO 93/13,148 can also be used. The above list of hot-melt pressure-sensitive adhesives is only explanatory and not limiting, and other hot-melt pressure-sensitive adhesives may also be used. The person skilled in the art can easily select hot-melt pressure-sensitive adhesives useful in the present invention from the group of adhesives mentioned above as well as from the pool of hot-melt pressure-sensitive adhesives available in the prior art, by determining the viscosity at the respective coating temperature and preferably additionally the 1800 peel adhesion as described above, The coating temperature preferably is between ISO and 180° C. and more preferably between 160 and 180° C.

Especially suitable is Lunamelt PS 4151 which is a synthetic rubber based hot-melt pressure-sensitive adhesive commercially available from H- B- Fuller Company. Minneapolis, Minn., U.S.A.

It was furthermore found by the present inventors that the density of hook elements on the backing layer 1 of the mechanical fastening element preferably is less than 2,000 hook elements per square inch and, in particular, less than 1,500 hook elements per square inch in order to avoid formation of adhesive bridges between adjacent hook heads 3. The density of the hook elements on the backing layer 1 of the mechanical fastening element preferably is at least 200 hook elements per square inch and, more preferably, at least 500 hook elements per square inch in order to allow for a reliable mechanical engagement between the mechanical hook and the complementary fastening element. The average distance between two adjacent hook heads 3 preferably is more than 200 gm and more preferably at least 300 gm. The average distance between two adjacent hook heads preferably is less than 2 mm and, in particular, less than 1 mm.

It was furthermore found by the present inventors that the coating pattern of the hot-melt pressure-sensitive adhesive 5 on the mechanical hook fastening element can be controlled by adjusting the orientation of the coating head 6 with respect to the continuous sheet 7 of the uncoated mechanical hook fastening element and the coating roll 8. The term coating head refers, for example, to the coating head of a hot melt slot orifice coater comprising a die 10. Slot orifice coaters are described, for example, in Handbook of Pressure Sensitive Adhesive Technology, ed. by Donatas Satas, 2nd edition, New York 1989, pp. 795–798.

Figure 3:
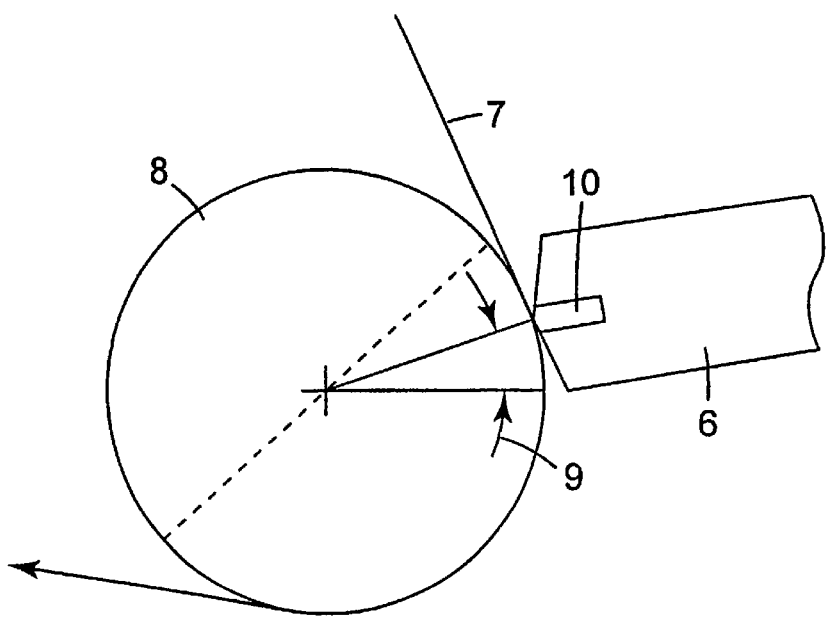
FIG. 3 is a schematic representation of a specific coating equipment useful for manufacturing the mechanical hook fastening element according to the invention, said equipment comprising a coating head 6 for applying the hot-melt pressure-sensitive adhesive 5, and a continuous sheet 7 of a mechanical hook fastening element which is fed to coating roll 8 thereby passing coating head 6, the angle 9 between a line connecting the center of the coating roll 8 and the die 10 of the coating head 6, and the horizontal direction being chosen sufficiently high to coat the hot-melt pressure-sensitive adhesive 5 essentially only onto at least part of top portions of the hook heads.

In the schematic representation of FIG. 3 the continuous sheet 7 of the uncoated mechanical hook fastening element is fed onto the coating roll 8 thereby passing the coating head 6 having a die 10. It was found that the coating configuration of FIG. 3 exhibiting a sufficiently high angle 9 between a line connecting the center of the coating roll 8 and the die 10, and the horizontal direction essentially favours the depositioning of the hot-melt pressure-sensitive adhesive 5 on the top part of the hook heads whereas the coating configuration of FIG. 4 tends to result in mechanical hook fastening elements exhibiting hot-melt pressure-sensitive adhesive 5 both on the hook heads and in the interstitial spaces 4 between the stems 2. The coating configuration of FIG. 3 thus tends to provide coated mechanical hook fastening elements similar to that of FIG. 1 whereas the coating configuration of FIG. 4 rather provides coated mechanical hook fastening elements similar to that of FIG. 2.

Although the present inventors do not wish to be bound by such theory it is assumed that selecting the angle 9 between a line connecting the center of the coating roll 8 and the die 10, and the horizontal direction to be sufficiently high effects that the sheet 7 when being contacted by the coating head 6 by exerting a suitable application force onto the coating head 6, is not or is only slightly pressed against the coating roll 8, The counter-pressure exerted by the sheet 7 and/or the coating roll onto the coating head 6 therefore is relatively low and results in favouring of coating patterns similar to that of FIG. 1. Contrary to this, in the configuration of FIG. 4, the counter-pressure exerted by the sheet 7 and/or the coating roll 8 onto the coating head 6 is higher, and coating patterns similar to that of FIG. 2 are favoured.

These findings which are essentially described above and below in terms of slot orifice coating equipment, can easily and without any inventive effort be transferred to other hot-melt pressure-sensitive adhesive coating equipment such as, for example, extrusion coaters, roll coaters or spray coaters such as adhesive meltblown systems, available, for example, from J&M Laboratories, Atlanta or Nordson Corp., Norcross, Ga. U.S.A.

Figure 4:
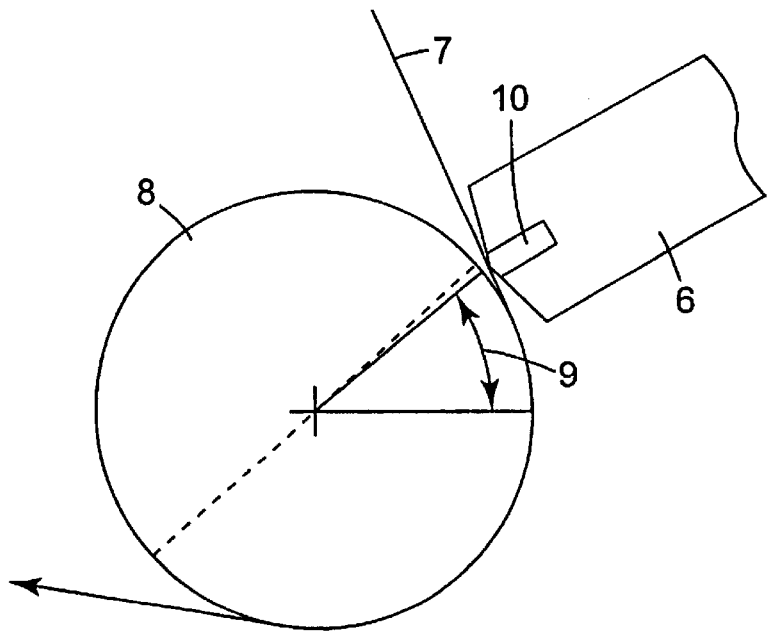
FIG. 4 is a schematic representation of a specific coating equipment useful for manufacturing the mechanical hook fastening element according to the invention, said equipment comprising a coating head 6 for applying the hot-melt pressure-sensitive adhesive 5, and a sheet 7 of a mechanical hook fastening element which is fed to coating roll 8 thereby passing coating head 6, the angle 9 between a line connecting the center of the coating roll 8 and the die 10 of the coating head 6, and the horizontal direction being chosen sufficiently low to coat the hot-melt pressure-sensitive adhesive 5 essentially onto the top portion of at least some hook heads and/or at least part of the -interstitial spaces 4 between the adjacent stems 2.

The coating configurations shown in FIGS. 3 and 4 can be easily modified based on the teaching of the present invention, to provide various other coating patterns. If, for example, a gradually increasing amount of the hot-melt pressure-sensitive adhesive 5 is required in cross-direction, a continuously curved coating head 6 may be used whereby he position of the die 10 at one end of the sheet 7 in cross-direction corresponds to at of FIG. 3 and at the other end of the sheet 7 in cross-direction to that of FIG. 4.

The level of the hot-melt pressure-sensitive adhesive deposited on the hook heads 3 d/or in the interstitial spaces 4 between the stems is further controlled by the coating weight which preferably is between 5 and 50 g/cm$^2$ and more preferably between 10 and 35 g/cm$^2$.

The hot-melt pressure-sensitive adhesive coated mechanical hook fastening elements of the present invention are suitable for various applications and, in particular, for use in closure tabs of disposable garments such as diapers or hospital gowns.

The construction of a diaper and the positioning of the closure tabs on the edge portions of a diaper is described to some detail in the corresponding European patent placation no, 97112042.3 filed by the present applicant. A closure tab comprising a hot-melt pressure sensitive adhesive coated mechanical fastening element according to the invention, is secured to the outer and optionally also to the inner surface of each of the two edge portions of the diaper with its manufacturer's end. The sure tape is preferably additionally adhered to the inside surface of the diaper with a release sheet having an exposed polymeric surface with release properties and bearing an adhesive layer on the other side. This anchoring mode which is usually referred to as shear mode or Y mode attachment, reliably secures the closure tab to the edge portion of the diaper.

The first hot-melt pressure-sensitive adhesive coated mechanical hook fastening element is located at the user's end of the closure and is engagable with the second mechanical fastening element in the landing zone of the diaper in order to allow for securing of the diaper around the wearer's body during the use. The attachment mechanism between the first and second mechanical fastening element preferably mainly relies on the mechanical engagability of the two fastening elements but can also use a combination of the mechanical and adhesive functionality of the first fastening element.

Prior to use, the diaper is usually stored in a folded form and the user's end of the closure tab is folded in case of a Y mode type of attachment to contact the release liner securing the closure tab to the inner surface of the diaper. In this case, the first mechanical fastening element preferably exhibits hot-melt pressure sensitive adhesive 5 on the top portions of at least some hook heads 3 in order to releasably adhere the closure tab to the release tape, thus preventing the closure tab from "popping open".

The closure tab can, however, also be attached during the storage stage to the inner surface of the diaper which may be made from a wide range of liquid pervious, compliant, soft feeling and non-irritating materials, comprising, for example, porous foams, reticulated foams, apertured films, natural fibers (e.g. wood or cotton fibers), synthetic fibers (e.g., polyester or polypropylene fibers) or combinations of natural and synthetic fibers. The inner surface may be manufactured by various methods and may be, for example, woven, non-woven, spunbonded, carded or hydroformed. In case the closure tab is only adhered, for example, to the outer surface of the diaper, the first adhesive coated mechanical fastening element may be adhered in the storage state also o the inner surface of the diaper, mainly using the mechanical functionality or a combination of the mechanical and adhesive functionality of the first fastening element cording to the invention. The closure tab may he adhered in an alternative embodiment to the inside surface of the diaper with an adhesive tape having, for example, a nonwoven exposed surface instead of the release surface, In this case, the first adhesive coated fastening element may be adhered to the non-woven surface of this fastening tape, mainly using the mechanical functionality or a combination of the mechanical and adhesive functionality of the first fastening element according to the invention.

After use, when the soiled diaper is rolled up for disposal, the diaper is preferably secured in this state to be conveniently disposable. The absorbent article therefore preferably comprises a disposability feature which may be realized in the absorbent article according to the invention in various different ways depending on the construction of the diaper.

The outside surface of the diaper may be a thin plastic film such as, for example, a polyolefin film such as polyethylene. In this case, the first mechanical fastening element preferably exhibits hot-melt pressure sensitive adhesive 5 on the top portions of at least some hook heads 3 in order to reliably adhere the closure tab to the outside surface of the diaper, thus securing the diaper in the rolled-up state.

The outside surface of the diaper may also comprise on top of a liquid impervious material an additional layer of a compliant, soft feeling and non-irritating material which may be selected, for example, from the group of materials listed above for the inner or inside surface. As noted above for- the inner surface, such outer layer may be manufactured by various methods and may be, for example, woven, non-woven, spunbonded, carded or hydroformed. In this case, the first adhesive coated fastening element may be adhered to the outside surface of the diaper in the rolled-up state, mainly using the mechanical functionality or a combination of the mechanical and adhesive functionality of the first fastening element according to the invention.

The absorbent article may also comprise a third mechanical fastening element which is engagable with the first adhesive coated fastening element on the closure tab. The third fastening element may be attached to the outside surface of the diaper or may be located, for example, on the other closure tab, for example, on the surface of the closure tab opposite to the surface bearing the first mechanical closure system. In this case, the first adhesive coated fastening element may be adhered to the third mechanical fastening element, mainly using the mechanical functionality or a combination of the mechanical and adhesive functionality of the first fastening element according to the invention. The third fastening element preferably is an adhesive coated fastening element according to the invention. The hot-melt pressure-sensitive adhesive coated mechanical hook fastening element of the present invention thus

- prevents the closure tab in diapers from popping open,
- reliably secures the diaper onto the wearer's body and
- exhibits a disposability feature allowing for convenient disposal of the diaper and is thus especially well suited for use in disposable garments and, in particular, for diapers.

The following examples are to farther explain the invention without limiting it.

EXAMPLES

Example 1

A sheet of a mechanical hook fastening element comprising a polypropylene backing layer (100 μm thick) and mushroom-type hooks (hook height—0.55 mm, stem width—0.26 mm, hook head diameter.—0.44 mm) with a density of 900 hooks per square inch which is commercially available under the trade designation XMH-4123 from 3M Company, St. Paul, U.S.A., was passed over a rubber roll with a diameter of 80 mm with the backing layer of the substrate facing the roll and the book-bearing surface of he sheet being exposed to the die of a hot melt slot orifice coating head in a configuration similar to that of FIG. 4. The angle between a line connecting the center f the roll and the die and the horizontal direction was approximately 10–20°. The sheet speed was set at approximately 200 m/min, The hot-melt pressure-sensitive hesive applied to the hooks was commercially available as LUNAMELT PS 4151 BS block copolymer and tackifying resin) from H. B. Fuller (Minneapolis, Minn., U.S.A.). The viscosity of the hot-melt adhesive (measured at 175° C. according to DTN 53018 with a rotovisco MVE 40) was between 9,000 and 11,000 mPa.sec. The adhesive was applied to the sheet to give a coating weight of 20 g/m².

The adhesive coated mechanical hook fastening element was examined both visually and with an optical microscope. Adhesive was present on top of the hook heads as well as in between the stems. Viewing with an optical microscope showed little bridging of adhesive between adjacent hook heads less than about 5%. Qualitative tests were made by contacting the adhesive-coated mechanical hook fastening element with a loop designed to function with the uncoated mechanical hook fastening element as a mechanical fastening system. The adhesive coated mechanical hook fastening element was still able to engage the loop material and function as a mechanical fastening system.

Comparative Example 1

Example 1 was repeated except that AG-1092, a synthetic rubber-based hot-melt pressure-sensitive adhesive available from 3M Company, St. Paul, Minn., U.S.A. was used. The viscosity was 22,000 mPa-s at 180° C.

The adhesive-coated mechanical hook fastening element was examined both visually and with an optical microscope. The adhesive formed clots covering larger areas of the hook structure. The coated mechanical hook fastening element no longer functioned as a mechanical fastening element.

Comparative Example 2

Example 1 was repeated except that Dispofix 625E from National Starch and Chemical GmbH, Neustadt, Germany, was used as a hot-melt pressure-sensitive adhesive, This adhesive has a viscosity of about 1,600 mpa-s at 160° C.

The adhesive-coated mechanical hook fastening element was examined both visually and with an optical microscope, Adhesive was visible both between the stems and on top of the hooks. Little or no anchorage was obtained between the adhesive coated mechanical hook fastening element and a mechanical loop fastening element engagable with the uncoated hook fastening element and the coated mechanical hook fastening element no longer functioned as a mechanical fastening element.

Comparative Example 3

Example 1 was repeated with the exception that a sheet of a mechanical hook fastening element comprising a polymer backing (thickness 85 μm) and mushroom-type hooks with a density of 2,500 hooks per square inch (hook height, 0.32 mm, stem width: 0.20 mm, hook head diameter, 0.36) which is commercially available under the trade designation RMH-001 from 3M Company, St. Paul, Minn., U.S.A., was used as a mechanical hook fastening element. Examination of the coated substrate showed substantial bridging of adhesive between heads of adjacent hooks, presenting a nearly homogenous coating of pressure-sensitive adhesive covering the entire hook structure, The coated mechanical hook fastening element no longer functioned as a mechanical fastening element.

What is claimed is:

1. A mechanical fastening element comprising a multiplicity of flexible hook elements emanating from a backing layer (1) and comprising stems (2) terminating in hook heads (3), said fastening element being releasably engagable with a complementary mechanical fastening element, top portions of at least some hook heads (3) and/or at least part of interstitial spaces (4) between stems (2) of said hook elements being coated with a hot-melt pressure-sensitive adhesive (5) so that the level of the adhesive in the interstitial spaces (4), where present, does not exceed the length to the stems (2), and so that essentially no adhesive bridges are present between adjacent hook heads (3), said hot-melt pressure sensitive adhesive (5) having a viscosity as measured at the coating temperature of between 2,000 and 18,000 mPa-s.

2. Mechanical fastening element according to claim 1 wherein the hot-melt pressure-sensitive adhesive has a 180° peel adhesion of between 10 and 50 N/25 mm.

3. Mechanical fastening element according to claim 1 having a density of the hook elements on the backing layer (1) of from 200 to 2,000 hook elements per square inch.

4. Method of manufacturing a mechanical fastening element according to claim 1 comprising passing a sheet (7) of a mechanical fastening element comprising a multiplicity of flexible hook elements emanating from a backing layer (1) and comprising stems (2) terminating in hook heads (3), by a coating head (6) with the hook heads (3) facing the coating head (6), applying a hot-melt pressure sensitive adhesive (5) having a viscosity as measured at the coating temperature of between 2,000 and 18,000 mPa-s, to the sheet (7) by means of the coating head (6), orienting the coating head (6) with respect to the sheet of the mechanical fastening element so that the hot-melt pressure sensitive adhesive is coated to the top portions of at least some of the hook heads (3) and/or at least into part of the interstitial spaces (4) between the stems (2) of said fastening elements so that the level of the adhesive in the interstitial spaces (4) where present does not exceed the length of the stems (2) and essentially no adhesive bridges are present between the heads (3).

5. Absorbent article, particularly a disposable diaper, comprising a closure tab on each edge portion of the diaper comprising a first mechanical fastening element according to claim 1, said first mechanical fastening element being releasably engagable with a second mechanical fastening element on the landing zone of the outside surface of the diaper which is complementary with the first mechanical fastening element, said first mechanical fastening element being adhesively and/or mechanically attachable to other portions of the outside surface of the diaper or to a third mechanical fastening element on the outside surface of the diaper or on the other closure tab whereby the third mechanical fastening means is complementary with the first mechanical fastening element, said adhesive attachment being obtained by means of the hot-melt pressure-sensitive adhesive (5) present on at least part of the hook heads (3) and/or in at least part of the interstitial spaces (4) between the stems (2) of said first mechanical fastening element and said mechanical attachment being obtained by mechanically engaging the first mechanical fastening element with the outside surface of the diaper or the third mechanical fastening element.

6. Absorbent article according to claim 5 wherein the third mechanical fastening element is multiplicity of flexible hook elements emanating from a backing layer (1) and comprising stems (2) terminating in hook heads (3), said fastening element being releasably engagable with a complementary mechanical fastening element, top portions of at least some hook heads (3) and/or at least part of interstitial spaces (4) between stems (2) of said hook elements being coated with a hot-melt pressure-sensitive adhesive (5) so that the level of the adhesive in the interstitial spaces (4), where present, does not exceed the length of the stems (2), and so that essentially no adhesive bridges are present between adjacent hook heads (3), said hot-melt pressure sensitive adhesive (5) having a viscosity as measured at the coating temperature of between 2,000 and 18,000 mPa-s.

7. Closure tab for an absorbent article, particularly for a disposable diaper, for fastening of the article on the body of a person, said tab comprising a mechanical fastening element according to claim 1.

* * * * *